United States Patent [19]

Lösel et al.

[11] Patent Number: 5,688,793

[45] Date of Patent: Nov. 18, 1997

[54] PYRIDAZINO[4',5':3,4]PYRROLO-[2,1-A]-ISOQUINOLINES AND THE USE THEREOF FOR PREPARING PHARMACEUTICAL PREPARATIONS

[75] Inventors: Walter Lösel, Gau-Algesheim; Otto Roos, Schwabenheim; Dietrich Arndts, Appenheim, all of Germany

[73] Assignee: Boehringer Ingelheim GmbH, Ingelheim am Rhein, Germany

[21] Appl. No.: 699,809

[22] Filed: Aug. 19, 1996

Related U.S. Application Data

[63] Continuation of Ser. No. 360,863, Dec. 21, 1994, abandoned.

[30] Foreign Application Priority Data

Dec. 21, 1993 [DE] Germany .............. 43 43 649.8

[51] Int. Cl.$^6$ .................. A61K 31/50; C07D 487/04
[52] U.S. Cl. .................. 514/248; 544/233
[58] Field of Search .................. 544/233; 514/248

[56] References Cited

U.S. PATENT DOCUMENTS 4,694,085  9/1987  Lösel et al. .................. 546/65

5,614,516  3/1997  Lösel et al. .................. 514/233.2

FOREIGN PATENT DOCUMENTS 1256432  6/1989  Canada.

*Primary Examiner*—Emily Bernhardt
*Attorney, Agent, or Firm*—Robert P. Raymond; Alan R. Stempel; Mary-Ellen Devlin

[57] ABSTRACT

The invention relates to new pyridazino[4',5':3,4]-pyrrolo[2,1-a]isoquinolines of the formula

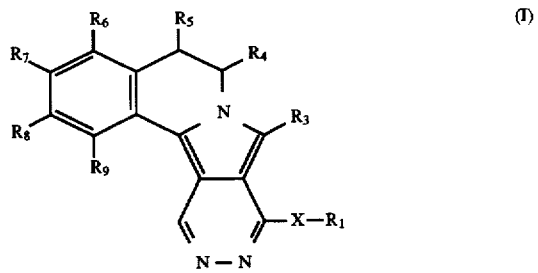

and the physiologically acceptable salts thereof with acids and complex-forming agents, wherein X is O, S or NHO and $R_1$, $R_3$, $R_4$, $R_5$, $R_6$, $R_7$, $R_8$ and $R_9$ are defined as in the specification, and pharmaceutical preparations containing these compounds.

20 Claims, No Drawings

PYRIDAZINO[4',5':3,4]PYRROLO-[2,1-A]-ISOQUINOLINES AND THE USE THEREOF FOR PREPARING PHARMACEUTICAL PREPARATIONS

This is a continuation of application Ser. No. 08/360,863, filed Dec. 21, 1994, now abandoned.

From German Patent Applications DE 35 00 941.1 and DE-35-25-048-8, cardiotonically active 9-amino-pyridozino [4',5':3,4] pyrrolo- [2,1-a]isoquinolines are known. It is known from European Patent Application No. 252-299(A) that these compounds have cardio- and neuroprotective effects and additionally promote blood circulation to the tissues and the supply of oxygen to the tissues in the central nervous system.

The invention relates to new pyridazino[4',5':3,4]-pyrrolo[2,1-a]isoquinolines of formula I

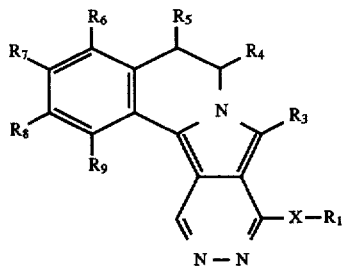

and the physiologically acceptable salts thereof with adds and complex-forming agents. The new compounds have valuable therapeutically useful properties. They may be used as cardioprotective agents, as cerebroprotective agents (particularly for treating patients who have suffered a stroke or are in danger of suffering a stroke) and as agents for treating chronically inflammatory processes (e.g. bronchial asthma and arthritis). These compounds may also be used as agents with an antiproliferative effect and as agents for treating ulcerative colitis and Crohn's disease.

In formula I:

X represents O,S or NHO;

$R_1$ has one of the following meanings:

a) a heterocyclic 5- or 6-membered ring containing a nitrogen atom and optionally, as a further heteroatom, an oxygen, nitrogen or sulphur atom;

b) $C_{3-7}$-cycloalkyl;

c) a straight-chained or branched, saturated or unsaturated alkyl group having 1 to 10 or 2 to 10 carbon atoms, which may be substituted by hydroxy, $C_{1-4}$-alkoxy, halogen, $NH_2$, NH-alkyl having 1 to 2 carbon atoms, N,N-di($C_{1-2}$)alkylamino, NH-acyl having 2 to 4 carbon atoms, 1 or 2 $C_{3-7}$-cycloalkyl groups, phenoxy, 1 or 2 phenyl groups (wherein the phenyl ring or rings or phenoxy may in turn be mono- or disubstituted by halogen, $CF_3$, $C_1$-alkyl, $C_{1-2}$-alkoxy, NH-alkyl having 1 to 2 carbon atoms, N,N-dialkyl having 1 to 2 carbon atoms, $NH_2$, N-acyl having 2 to 3 carbon atoms, $-OCH_2O$, alkylsulphonylamino, phenoxy or benzyloxy), furyl, thienyl, a nitrogen-containing heterocyclic 5- or 6-membered ring which may optionally contain an oxygen or sulphur atom as a further heteroatom (wherein the ring may optionally be substituted by $C_{1-4}$-alkyl);

$R_3$, $R_4$ and $R_5$, which may be identical or different, represent hydrogen or a $C_{1-4}$-alkyl group;

$R_7$ and $R_8$, which may be identical or different, represent hydroxy; $C_{1-4}$-alkoxy; or $C_{1-4}$-alkylthio;

$R_6$ and $R_9$, which may be identical or different, represent hydrogen; hydroxy; $C_{1-4}$-alkoxy; $C_{1-4}$-alkylthio; or 2 adjacent substituents of the substituents $R_6$, $R_7$, $R_8$ and $R_9$ together form the group $-O-(CH_2)_{1 \text{ or } 2}-O-$ and the other 2 substituents are as hereinbefore defined. This excludes compounds of formula I as hereinbefore defined wherein $XR_1$ represents the group $SCH_3$. These compounds are known as starting compounds for preparing similar compounds (DE 35 00 941).

Particular mention should be made of compounds of formula I wherein X is as hereinbefore defined, $R_1$ has one of the following meanings:

a) a heterocyclic 5- or 6-membered ring containing a nitrogen atom and optionally, as a further heteroatom, an oxygen, nitrogen or sulphur atom;

b) $C_{3-7}$-cycloalkyl;

c) a straight-chained or branched, saturated or unsaturated alkyl group having 1 to 5 or 2 to 5 carbon atoms, which may be substituted by hydroxy, $C_{1-4}$-alkoxy, halogen, $NH_2$, NH-alkyl having 1 to 2 carbon atoms, N,N-di($C_{1-2}$)alkylamino, NH-acyl having 2 to 4 carbon atoms, $C_{3-7}$-cycloalkyl, phenyl (wherein the phenyl ring may in turn be mono- or disubstituted by halogen, $C_{1-2}$-alkyl, $C_{1-2}$-alkoxy, NH-alkyl having 1 to 2 carbon atoms, N,N-dialkyl having 1 to 2 carbon atoms, $NH_2$, N-acyl having 2 to 3 carbon atoms or ($C_1$ or $C_2$) alkylsulphonylamino), furyl, thienyl, a nitrogen-containing heterocyclic 5- or 6-membered ring which may optionally contain as a further heteroatom an oxygen or sulphur atom (whilst the ring is optionally substituted by $C_{1-4}$-alkyl);

$R_3$, $R_4$ and $R_5$, which may be identical or different, represent hydrogen or a $C_{1-4}$-alkyl group;

$R_7$ and $R_8$, which may be identical or different, represent hydroxy; $C_{1-4}$-alkoxy; or $C_{1-4}$-alkylthio and $R_6$ and $R_9$, which may be identical or different, represent hydrogen; hydroxy; $C_{1-4}$-alkoxy; $C_{1-4}$-alkylthio.

Particular mention should also be made of compounds (I) wherein $R_1$ is a straight-chained or branched $C_{1-4}$-alkyl group which is substituted by $C_{3-7}$-cycloalkyl, thienyl or 1 or 2 unsubstituted phenyl groups or by a substituted phenyl group the substituent(s) of which is or are defined as in claim 1 or 2, particularly those wherein $R_1$ is ($C_{1-4}$)alkylcyclcyclohexyl, preferably $-CH_2-C_6H_{11}$, or wherein $R_1$ is ($C_{1-4}$)alkylphenyl, wherein the phenyl group is unsubstituted or is mono- or disubstituted by F, Cl, $CF_3$, methyl, ethyl, methoxy or ethoxy.

Particular mention should be made of compounds (I) wherein $R_1$ is one of the following groups:

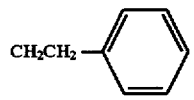

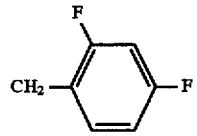

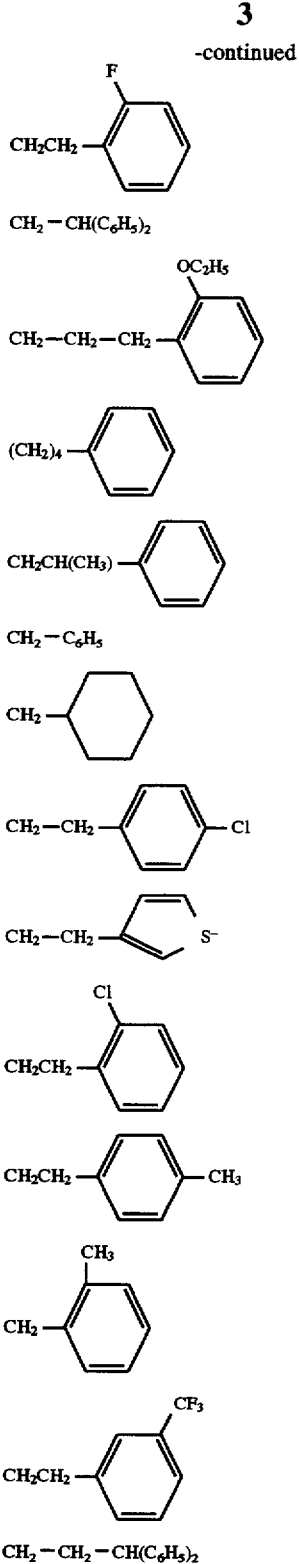

particularly those wherein $R_1$ is one of the following groups:

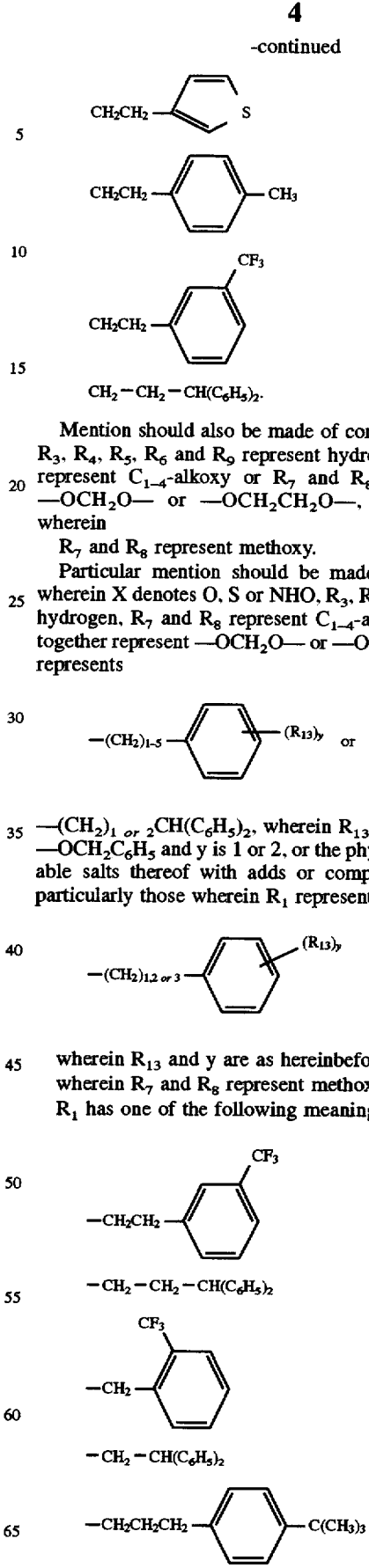

Mention should also be made of compounds (I) wherein $R_3$, $R_4$, $R_5$, $R_6$ and $R_9$ represent hydrogen and $R_7$ and $R_8$ represent $C_{1-4}$-alkoxy or $R_7$ and $R_8$ together represent —OCH$_2$O— or —OCH$_2$CH$_2$O—, particularly those wherein $R_7$ and $R_8$ represent methoxy.

Particular mention should be made of compounds (I) wherein X denotes O, S or NH, $R_3$, $R_4$, $R_5$, $R_6$ and $R_9$ are hydrogen, $R_7$ and $R_8$ represent $C_{1-4}$-alkoxy or $R_7$ and $R_8$ together represent —OCH$_2$O— or —OCH$_2$CH$_2$O— and $R_1$ represents —(CH$_2$)$_{1\text{-}5}$—〈phenyl〉—(R$_{13}$)$_y$  or —(CH$_2$)$_{1\text{ or }2}$CH(C$_6$H$_5$)$_2$, wherein $R_{13}$ is CF$_3$, C(CH$_3$)$_3$ or —OCH$_2$C$_6$H$_5$ and y is 1 or 2, or the physiologically acceptable salts thereof with acids or complex-forming agents, particularly those wherein $R_1$ represents the group —(CH$_2$)$_{1,2\text{ or }3}$—〈phenyl〉—(R$_{13}$)$_y$ wherein $R_{13}$ and y are as hereinbefore defined and/or wherein $R_7$ and $R_8$ represent methoxy and/or $R_1$ has one of the following meanings

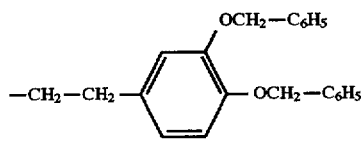
particularly those wherein $R_1$ has one of the following meanings:
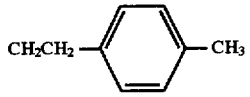
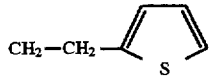
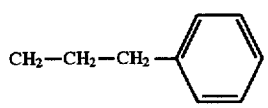
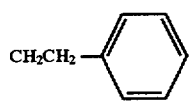
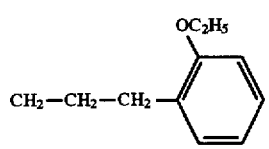
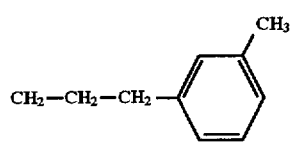
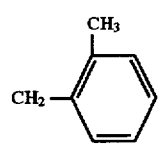
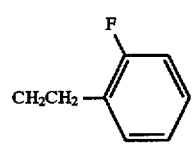
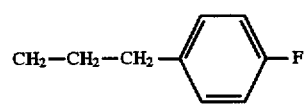
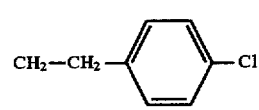
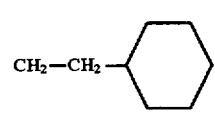
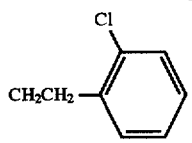
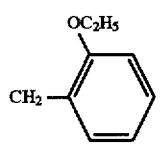
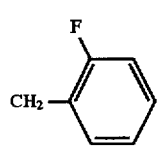
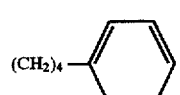
preferably wherein $R_1$ has one of the following meanings:
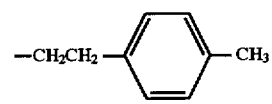
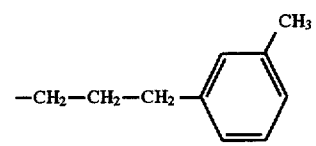
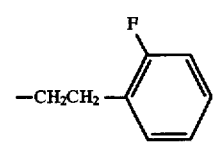
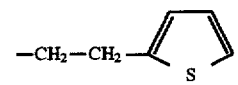
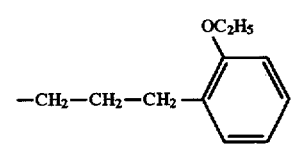
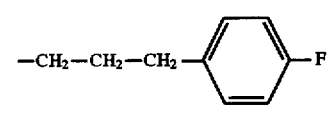
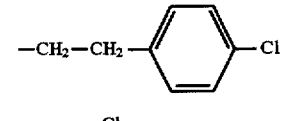
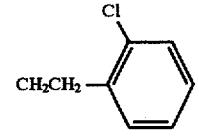

-continued

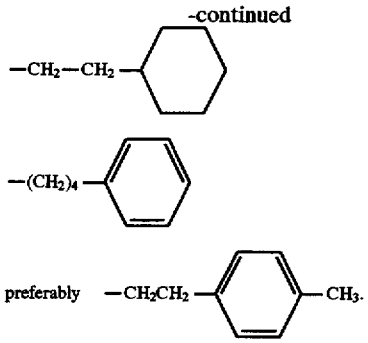

preferably —CH₂CH₂—⟨phenyl⟩—CH₃.

Also preferred are those compounds of general formula I wherein $R_1$ denotes a straight-chained or branched $C_{1-5}$-alkyl group; methoxy-$C_{1-4}$-alkyl; cyclopropyl; cyclopentyl; cyclohexyl; cyclopropylmethyl; cyclohexylmethyl; phenylethyl, wherein the phenyl ring may optionally be mono- or disubstituted by methoxy, $CF_3$ or halogen; propargyl; (furan-2-yl)methyl; thienylmethyl; 2-hydroxyethyl; (pyridin-4-yl)-ethyl; benzyl; 3,3-diphenylpropyl; (thien-3-yl)ethyl; 4-phenylbutyl;

and $R_7$ and $R_8$ independently of each other represent hydrogen; methyl; methoxy; hydroxy; or methylthio and $R_3$, $R_4$, $R_5$, $R_6$ and $R_9$ represent hydrogen.

The compounds of formula I are bases and may be converted in the usual way with inorganic or organic acids and salt and complex-forming agents into any desired physiologically acceptable adducts (salts).

Acids suitable for salt formation include, for example, hydrochloric acid, hydrobromic acid, hydriodic acid, hydrofluoric acid, sulphuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid, phthalic acid, cinnamic acid, salicylic acid, ascorbic acid, methanesulphonic acid and the like.

Preferred compounds of general formula I are those wherein $R_3$, $R_4$, $R_5$, $R_6$ and $R_9$ represent hydrogen and $R_7$ and $R_8$ represent methoxy, and/or $R_1$ represents a group —$(CH_2)_{0-5}$—A, wherein A is cyclopentyl, cyclohexyl, phenyl, phenyl which is mono- or disubstituted by F, Cl, $CH_3$, $CF_3$, $OCH_3$ or $OC_2H_5$,

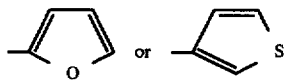

The new compounds may be prepared by methods known per se.

The new compounds of formula I wherein X represents NHO may be obtained by reacting a compound of general formula II

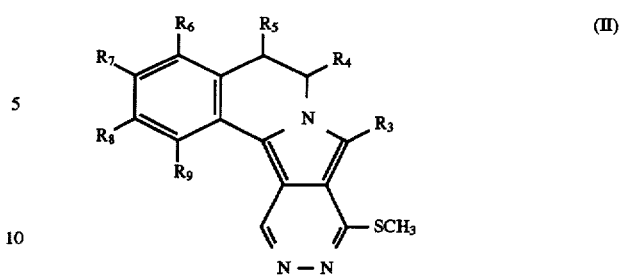

wherein the groups $R_3$, $R_4$, $R_5$, $R_6$, $R_7$, $R_8$ and $R_9$ are as hereinbefore defined, with a compound of general formula III $H_2N$—$OR_1$     (III)

wherein $R_1$ is as hereinbefore defined.

A starting compound of general formula II is dissolved in a high boiling inert solvent, such as dimethylformamide, dimethylacetamide, chlorobenzene or hexamethylphosphoric acid triamide and refluxed with the amine component of general formula III until the reaction has ended. The reaction time is between about 1 and 15 hours and depends on the starting components used.

In the case of reactive hydroxylamines, alcohols or tetrahydrofuran may also be used as solvent; under certain circumstances it may be advantageous to carry out the reaction in an autoclave.

If the hydroxylamines used are liquid and sufficiently high-boiling, the reaction may also be carried out in an excess of the amine without any additional solvent (e.g. in the case of o-benzylhydroxylamine), optionally under a nitrogen atmosphere.

In some cases it may be possible to use a reactant which also acts as a solvent during the reaction.

The products of general formula I wherein X represents S or O may be obtained by reacting a compound of general formula IV

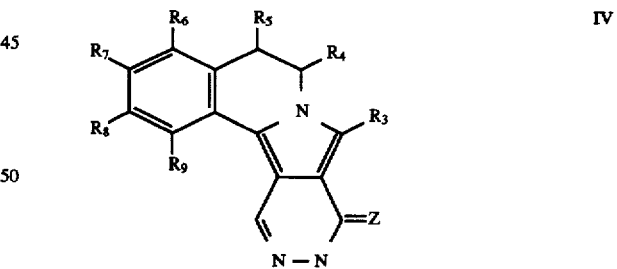

wherein the groups $R_3$, $R_4$, $R_5$, $R_6$, $R_7$, $R_8$ and $R_9$ are as hereinbefore defined and Z represents oxygen or sulphur, with an alkylating reagent of formula V $R_1$—Y     V wherein $R_1$ is as hereinbefore defined and Y denotes an anionic leaving group, e.g. Cl, Br, I, the methanesulphonic acid group, the trifluoromethane-sulphonic acid, p-toluenesulphonic acid, p-nitrobenzenesulphonic acid or p-bromobenzenesulphonic acid group. However, the alkylating agent may also consist of other reagents which are capable of transferring carbocations, e.g. "onium" compounds such as Meerwein salts, e.g. triethyloxonium-tetrafluoroborate, -phosphate or -hexachloroantimonate.

A starting compound of general formula IV is reacted with the alkylating agent of general formula V in an inert solvent, e.g. dimethylacetamide, hexamethylphosphoric acid triamide, chlorobenzene or acetone. The reaction is usually carried out at ambient temperature, occasionally at reflux temperature depending on the reactivity of the alkylating agent. The reaction time is between about 1 and 20 hours and depends on the starting components used.

The pyridazino-pyrrolo-isoquinolines (I) according to the invention are bases and may be converted in the usual way into any desired physiologically acceptable add addition salts with inorganic or organic adds.

Acids suitable for salt formation include, for example, hydrochloric acid, hydrobromic acid, hydriodic acid, hydrofluoric acid, sulphuric acid, phosphoric acid, nitric acid, acetic acid, propionic acid, butyric acid, caprole acid, valetic acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicylic acid, ascorbic acid and methanesulphonic acid.

EXAMPLES 1. 5,6-Dihydro-2,3-dimethoxy-9-(O-benzyl)-hydroxylaminopyridazino[4',5':3,4]pyrrolo[2,1-a]-isoquinoline hydrochloride 3 g of 5-methyl compound, 5 g of o-benzylhydroxylamine hydrochloride and 50 ml of toluene are refluxed for about 5 hours. After the reaction has ended (monitored by TLC) the mixture is cooled and the reaction product is suction filtered.

It is washed twice with toluene and divided between $CH_2Cl_2$ and dilute NaOH. The organic phase is washed several times with water, dried over $Na_2SO_4$ and evaporated down. The residue is taken up in a little $CH_2Cl_2$, optionally after purification over a silica gel column (eluant $CH_2Cl_2$/MeOH=100+10 V.V.) and converted into the hydrochloride by the addition of ethanolic HCl.

Yield 2.86 g (71.5% of theory).

2. 5,6-Dihydro-2,3-dimethoxy-9-(4-bromobenzyl)-mercaptopyridazino[4',5':3,4]pyrrolo[2,1-a]-isoquinoline 1.28 g of 5,6-dlhydro-2,3-dimethoxypyridazino-[4',5':3,4] pyrrolo[2,1-a]isoquinolin-9-(10H)thione are suspended in 30 ml of dimethylacetamide and at ambient temperature 3.50 g of 4-bromobenzylbromide are added with stirring. After about 20 minutes a clear, reddish-orange solution is formed from which orange crystals are precipitated as stirring continues at ambient temperature. The mixture is left to stand for 16 hours at ambient temperature, the crystals are suction filtered and dissolved in a mixture of methylene chloride and methanol (100+20). The mixture is washed first with dilute NaOH, then with water, dried over anhydrous sodium sulphate and evaporated down. The residue is crystallised from $CH_2Cl_2$:MeOH (100+20).

Yield 5.5 g (89.3% of theory).

3. 5,6-Dihydro-2,3,9-trimethoxypyridazino[4',5':3,4]-pyrrolo[2,1-a]isoquinoline

A suspension of 6.3 g of 5,6-dihydxo-2,3-dimethoxypyridazino[4',5':3,4]pyrrolo[2,1-a]-isoquinoline in 50 ml of dimethylacetamide is reacted at ambient temperature with 5 ml of freshly distilled methyliodide. After about 1 hour a dear solution is formed. This is stirred for a further 30 hours at 50° C., left to cool and then the yellow crystals precipitated are suction filtered and dissolved in a methylene chloride/methanol mixture (100+20). This is washed first with dilute NaOH and then with $H_2O$. The organic phase is dried over anhydrous $Na_2SO_4$ and concentrated by evaporation. The residue is dissolved in a $CH_2Cl_2$—MeOH mixture (100+20) and crystallised by the addition of ether.

Yield: 4.7 g (75.6% of theory) m.p.:>270° C.

The following Tables list compounds according to the invention which can be prepared analogously to the above Examples.

TABLE 1

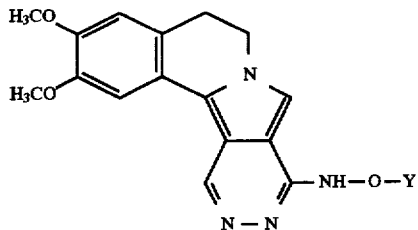

Y = —CH₃

—C₂H₅

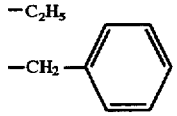

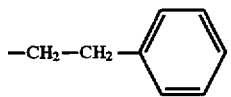

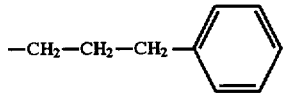

TABLE 2
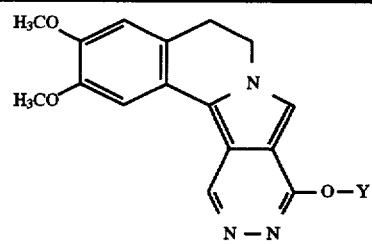
| Y = | —CH₃ (Mp. > 270° C.) | 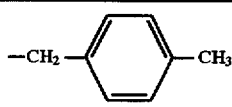 |
|---|---|---|
| | —C₂H₅ | 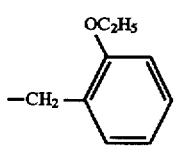 |
| | —CH₂—CH₂—CH₂—CH₂—CH₃ | 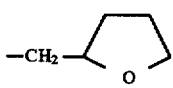 |
| | —CH₂—CH=CH₂ | |
| | —CH₂—C≡CH | 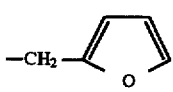 |
| | 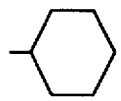 | 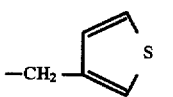 |
| | 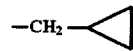 | 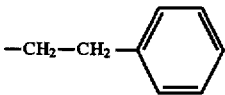 |
| | 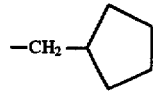 | 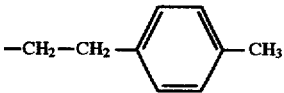 |
| | 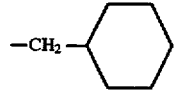 | 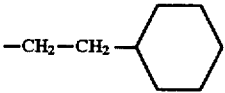 |
| | 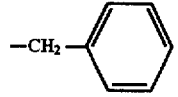 | 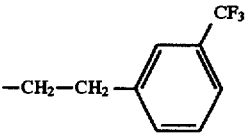 |
| | 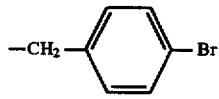 | 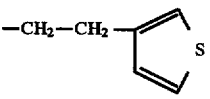 |
| | 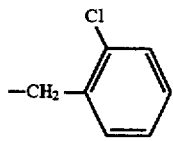 | 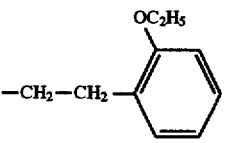 |

TABLE 2-continued
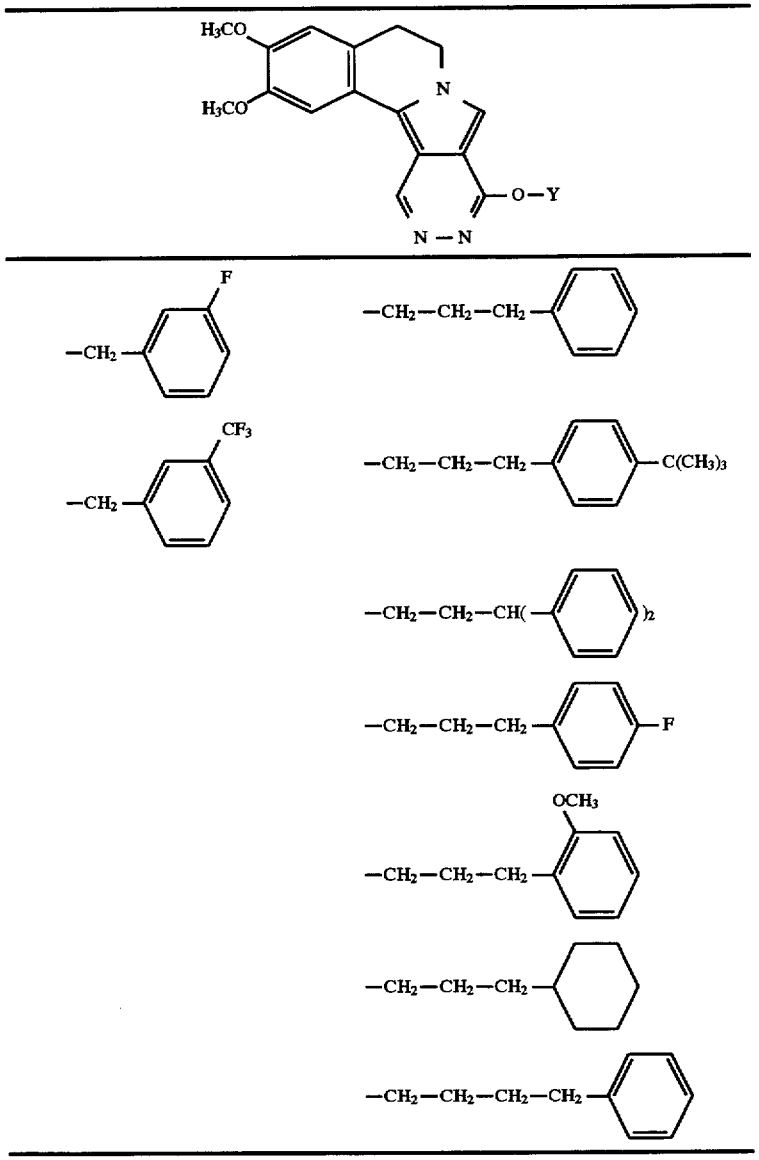
TABLE 3
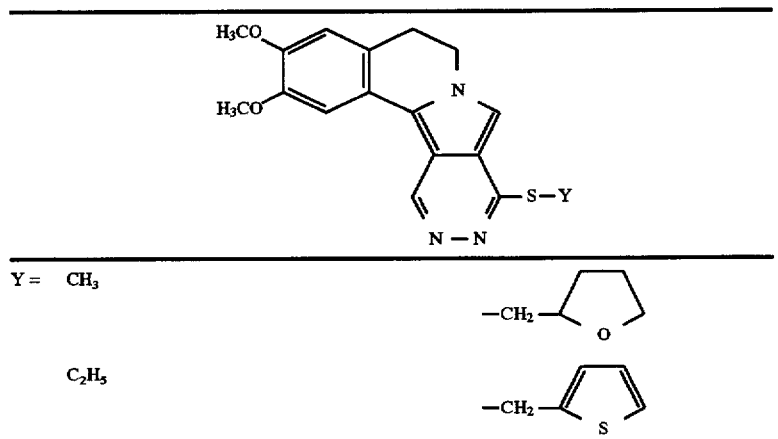

TABLE 3-continued
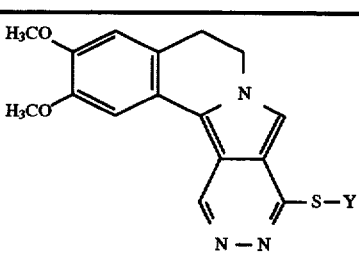
| | |
|---|---|
| —CH$_2$—CH(CH$_3$)$_2$ | |
| —(CH$_2$)$_3$—CH$_3$ | —CH$_2$—CH$_2$—C$_6$H$_{11}$ (cyclohexyl) |
| —CH$_2$—CH=CH$_2$ | —CH$_2$—CH$_2$—C$_6$H$_5$ |
| —CH$_2$—C≡CH | |
| —CH$_2$—CH$_2$—OC$_2$H$_5$ | —CH$_2$—CH$_2$—(2-CH$_3$-C$_6$H$_4$) |
| cyclopropyl | —CH$_2$—CH$_2$—(4-Cl-C$_6$H$_4$) |
| cyclohexyl | |
| —CH$_2$—cyclopropyl | —CH$_2$—CH$_2$—(3-F-C$_6$H$_4$) |
| —CH$_2$—cyclohexyl | |
| —CH$_2$—C$_6$H$_5$ (Mp. 204–205° C.) | —CH$_2$—CH$_2$—(3-CF$_3$-C$_6$H$_4$) |
| —CH$_2$—(4-CH$_3$-C$_6$H$_4$) | |
| —CH$_2$—(4-F-C$_6$H$_4$) (Mp. 190–192° C.) | —CH$_2$—CH$_2$—(3,4-methylenedioxyphenyl) |

TABLE 3-continued
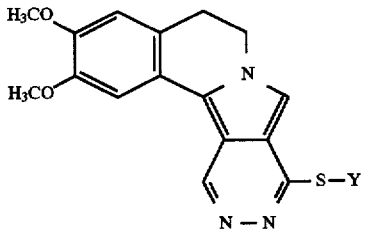
Y =
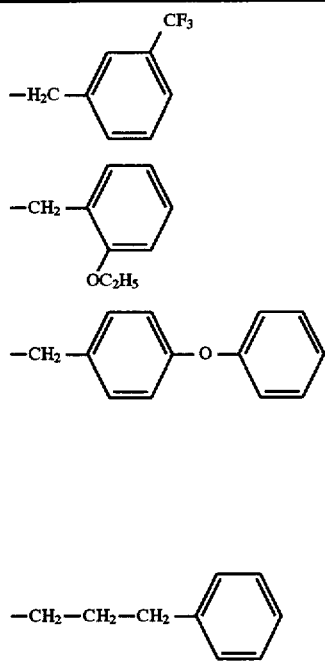
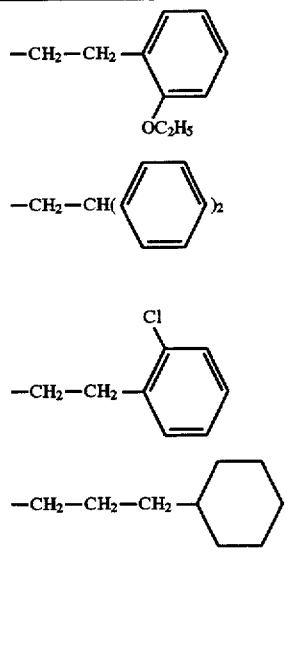
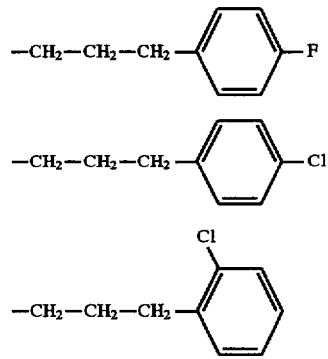
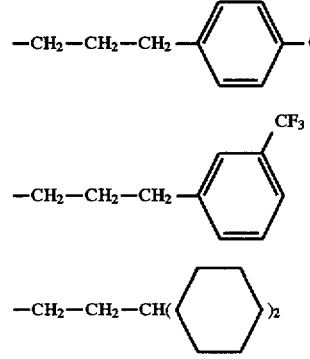

TABLE 3-continued

| Structure | Mp. (°C.) |
|---|---|
| (Core structure: 2,3-dimethoxy-substituted pyridazino-pyrrolo-isoquinoline with S—Y substituent) | |
| —CH₂—CH₂—CH(C₆H₅)₂ | |
| —CH₂—CH₂—CH₂—CH₂—C₆H₅ | |
| —CH₂—(2-CH₃-C₆H₄) | 183–185 |
| —CH₂—(2,6-Cl₂-C₆H₃) | 228 |
| —CH₂—CH₂—CH₂—CH₂—O—(2-F-C₆H₄) | 153–155 |
| —CH₂—(4-Br-C₆H₄) | 210 |
| —CH₂—(2-Cl-C₆H₄) | 200–202 |

The present invention relates to new 9-substituted pyridazino[4',5':3,4]pyrrolo[2,1-a]isoquinolines and pharmaceutical preparations containing these compounds.

The present invention also relates to the use of these new compounds.

The compounds are beneficial for treating degenerative and necrotising diseases of the brain. Preventive treatment of patients at risk of such diseases is also possible. The effect of the compounds is not based on an improvement in circulation of the blood through the tissues. The compounds are thus suitable for a novel treatment for epilepsy and Alzheimer's disease and particularly for the treatment of patients who have suffered a stroke or are at risk of suffering a stroke.

The present invention further relates to the use of the above compounds for preparing agents for the treatment of chronic inflammatory processes, ulcerative colitis and Crohn's disease and agents with an antiproliferative activity. The effect of the compounds can be explained by their inhibition of the unselective cation channels (UCC).

The pathophysiology of chronic bronchial asthma is based on inflammatory processes which are mediated by the activation of inflammatory cells. (BARNES, 1987; SEIFERT and SCHULTZ, 1991).

The receptor-regulated activation of inflammatory cells (e.g. neutrophilic granulocytes and mast cells or the permanent cell lines HL-60 cells or sensitised RBL cells, i.e. those charged with gammaglobulin E) is inhibited, irrespective of the nature of the stimulating agonists (e.g. endothelin, PAF, leukotrienes, chemotactical peptide fMLP or antigen against sensitised mast cells) by blockers of unselective cation channels (UCC) (RINK, 1990). Through these channels extracellular calcium, which is responsible for the persistence of receptor-mediated cell activations, enters the cells (PUTNEY, 1990). If this supply of calcium is interrupted, a blockade of the activation of inflammatory cells results.

Conventional calcium antagonists of the dihydropyridine or phenylalkylamine type do not inhibit either UCCs or inflammatory processes (WELLS et al., 1986).

As a measurement of the cell activation or as a measurement of the inhibition thereof by UCC blockers, the kinetics of the cytoplasmic calcium ion concentration in fura-2-charged cells is quantified fluorometrically using the method described by GRYNKIEWICZ et al. (1985). This procedure has proved a reliable screening method, within the scope of the invention, for detecting UCC blockers.

So-called functional THAPSIGARGIN inhibition has proved suitable for the specific characterisation of blockers of the unselective cation channels. THAPSIGARGIN is a rumour promoter described by THASTRUP et al. (Proc. Natl. Acad. Sci. (USA), 87, 2466–2470, 1990) which selectively and irreversibly inhibits the $Ca^{2+}$-ATPase of intracellular $IP_3$-sensitive $Ca^{2+}$-stores. Consequently the $Ca^{2+}$-stores are rapidly depleted. As described by J. PUTNEY (Calcium, 11, 611–624, 1990) the depletion of these stores constitutes the physiological stimulation for opening up unselective cation channels in the cell membrane. The result of this is a massive influx of $Na^+$ and $Ca^{2+}$ into the cell. Because of these properties, Thapsigargin is suitable as an indirect stimulator for agonist- and $IP_3$-independent opening up of the unselective cation channels.

Within the scope of the present invention the Thapsigargin stimulation of unselective cation channels has been carried out successfully on HL 60 cells (human leukaemia cells), on hippocampal and cortical neurone cells and on RBL-cells (rat basophilic lymphoma cells) and in this way the existence of these channels in particular cell lines was demonstrated.

The cytoplasmic $Ca^{2+}$ concentration ($[Ca^{2+}]_i$) plays an important part in the cell proliferation and in turnout growth (for a summary see L. R. ZACHARSKI, Journal of Medicine 19: 145–177, 1988). In particular, the $Ca^{2+}$-influx into the cell stimulated by receptor activation with consecutive inositoltriphosphate-($IP_3$-)-mediation would appear to be of crucial importance for oncogenic cell proliferation (U. KIKKAWA and Y. NISHIZUKA, Ann. REV. CELL. BIOL. 2: 149–178, 1986). This mechanism also plays a part in the formation of metastases and in "Multi-Drug Resistance". (For a summary see the above-mentioned publication by L. R. ZACHARSKI, J. MED. 19: 145–177, 1980).

This hypothesis is supported by the fact that Thapsigargin, as an indirect stimulator of the unselective cation channels (UCC) not only leads to a $Ca^{2+}$-overload in the cell but is also a highly effective turnout promoter. (V. THASTRUP et al. Proceedings of the NATL. Acad. Sci: (USA) 87: 2466–2470, 1990). The blockade of the $Ca^{2+}$-influx by the UCC leads to normalisation of the intracellular Ca-ion concentration and hence to inhibition of rumour growth etc.

Conventional calcium antagonists do not inhibit these UCC. It has been found, surprisingly, that the compounds according to this invention inhibit the influx of calcium into the cell through the UCC.

As shown by S. H. MURCH et al. (Lancet 339: 381–385, 15. February 1992) endothelin I plays an important pathophysiological role in inflammatory intestinal diseases such as ulcerative colitis and Crohn's disease. Using immunohistochemical methods it has been shown that patients with Crohn's disease in the region of the submucosa and patients with ulcerative colitis in the region of the lamina propria of the epithelium of the large intestine show significantly and greatly increased concentrations of endothelin I compared with healthy normal people. It is assumed that the local secretion of endothelin causes massive vasospasms with consecutive disseminated ischaemia with microinfarcts which are regarded as the actual cause of the above diseases. The vasospasmogenic effectiveness of endothelin is explained by a $Ca^{2+}$-overload of vascular myocytes. Endothelin primarily triggers an $IP_3$-mediated intracellular release of $Ca^{2+}$ which is followed by a massive transmembrane $Ca^{2+}$-entry through dihydropyridine-insensitive channels. (M. S. Simonson et al. Clin. Invest. Med. 14: 499–507, 1991; T. Masakai, J. Cardiovasc. Pharmacol. 13:Suppl. 5, S1-S4, 1989; D. W. Hay, R. J. Phamacol. 100: 383–392, 1990). These channels are unselective cation channels which have also been briefly described as existing in cells of the large intestine mucosa. (Chr. Siemer and H. Gögelein, Europ. J. Physiol. 420: 319–328, 1992).

The endothelin-stimulated activation of fura-2-charged human leukaemia cells (HL 60 cells) has proved a suitable screening model for detecting functional endothelin antagonists. In conformity with G. GRYNKIEWICZ et al. (J. Biol. Chem. 260:3440–3450, 1985) the intracellular $Ca^{2+}$-concentration in the cytoplasm of HL 60 cells (suspensions) can be monitored by spectrofluorometry and quantified as a measurement of cell activation by endothelin. The stimulation was effected by adding 0.1 mM endothelin and could be inhibited in a dosage-dependent manner by means of the substances according to the invention.

The functional endothelin antagonism of the substances according to the invention is mediated through a blockade of the unselective cation channels. Consequently, detection of a functional Thapsigargin-antagonism on RBL-hm1 cells is also a suitable screening method for functional endothelin antagonists.

Carrying out the investigation:

For screening purposes, fura-2-charged adhesive RBL-hm 1 cells are stimulated with 0.1 mM Thapsigargin in a $Ca^{2+}$-free incubation medium. After 4 minutes, extracellular $Ca^{2+}$ is restored to a concentration of 1.5 mM and, using the fura-2-fluorescence, the excessive increase in the cytoplasmic $Ca^{2+}$-concentration caused by a massive transmembranal $Ca^{2+}$-entry through unselective cation channels is recorded.

This entry is to be inhibited solely by unselective cation channel blockers in a dosage-dependent manner. Neither conventional calcium antagonists nor specific blockers of agonists which stimulate the $IP_3$-turnover are able to inhibit the transmembranal $Ca^{2+}$-entry triggered indirectly by Thapsigargin. The compounds of the present invention are distinguished by their inhibition of UCC.

The fluorometric calcium measurement in the cytoplasm of individual adhering RBL-hm1 cells is carried out analogously to the method described by KUDO and OGURA (1986) for neuronal cells. An AXIOVERT 35 fluorescence microscope made by ZEISS is used in conjunction with an imaging system made by HAMAMATSU, consisting of the ICMS-image processing system, residual light camera with control unit and image intensifier DVS 3000.

The kinetics of the cytoplasmic $Ca^{2+}$-concentration is recorded continuously as a concentration/time curve after the cell activation stimulated by Thapsigargin (0.1 µM). The curves of two activated cell cultures are compared in the presence and absence of 10 µM test substance. The area under these curves (area under the curve=AUC) is integrated and recorded as a measurement of cell activation. The inhibitory potency of the UCC-blockers tested is determined using the following equation:

$$\% H = 100 - \frac{AUC_{inh} \times 100}{AUC_{(control)}}$$

% H=the percentage inhibition of the calcium entry through unselective cation channels which is stimulated and inhibited by 10 μM of test substance.

$AUC_{inh}$=area under the curve recorded in the presence of the stimulant plus 10 μM inhibitory test substance.

AUC control=area under the curve which is recorded only after the addition of the stimulant.

Literature relating to the above explanations:

BARNES P. J., I. W. RODGER and N. C. THOMSON
Pathogenesis of asthma, in "ASTHMA, basic mechanisms and clinical management"
ED by P. J. BARNES; ACADEMIC PRESS, LONDON, 1988

GRYNKIEWICZ G., M. POENIE and R. Y. TSIEN
A new generation of $Ca^{2+}$-indicators with greatly improved fluorescence properties
J. BIOL. CHEM. 260: 3440–3450, 1985

HIDE, M. and M. A. BEAVEN
Calcium influx in a rat mast cell (RBL-2H3) line
J. BIOL. CHEM. 266 15221–15229, 1991

KUDO, Y. and A. OGURA
Glutmate-induced increase in intracellular $Ca^{2+}$-concentration in isolated hippocampal neurones
BR. J. PHARMACOL. 89: 191–198; 1986

PUTNEY, J. W., jr.
Capacitative Calcium entry revised
CELL CALCIUM 11: 611–624, 1990

RINK, T. J.
Receptor-mediated calcium entry
FEBS LETT. 268: 381–985, 1990

SEIFERT, R. and G. SCHULTZ
The superoxide forming NADPH oxidase of phagocytes: An enzyme system regulated by multiple mechanism
REV. PHYSIOL. BIOCHEM. PHARMACOL., Vol. 117, SPRINGER VERL., 1991

WELLS, E., C. G. JACKSON, S. T. HARPER, J. MANN and R. P. EAOY
Characterization of primate bronchoalveolar mast cells II, inhibition of histamine, $LTC_4$ and $PGF_{2\alpha}$ release from primate bronchoalveolar mast cells and a comparison with rat peritoneal mast cells
J. IMMUNOL. 137: 3941–3945, 1986.

Results of measurement:

The percentage inhibition of UCC after Thapsigargin stimulation (0.1 μM Thapsigargin) in RBL-hm 1 cells is given. The concentration of the test substances is $10^{-5}$ mol or $10^{-8}$ mol).

TABLE

RPL-hm 1 cells - Thapsigargin (0.1 μM) stimulation

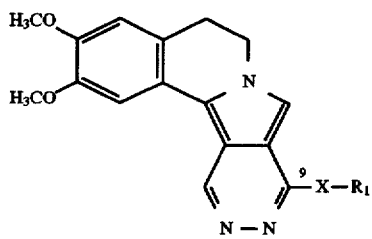

| $R_1$ (X:S) | % H ($10^{-5}$M) | % H ($10^{-6}$M) |
|---|---|---|
| —CH₂—C₆H₄(o-CH₃) | 21.8 | |
| —CH₂—C₆H₃(2,6-Cl₂) | 26.1 | |
| —CH₂—CH₂—CH₂—CH₂—O—C₆H₄(o-F) | 61.6 | |

TABLE-continued

RPL-hm 1 cells - Thapsigargin (0.1 μM) stimulation

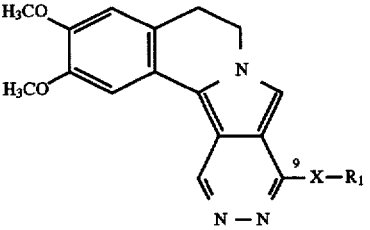

| | % H (10⁻⁵M) | % H (10⁻⁶M) |
|---|---|---|
| —CH₂—⟨C₆H₄⟩—Br | 62.9 | |
| —CH₂—⟨C₆H₄⟩—Cl (ortho) | 81.9 | 34.7 |
| —CH₂—⟨C₆H₄⟩—F | 94.6 | 52.9 |
| —CH₂—⟨C₆H₅⟩ | 97.5 | 56.1 |
| —CH₃  R₁ (X:O) | 46.4 | |
| —CH₃ | 62.5 | |

The functional antiinflammatory effectiveness can be demonstrated by means of the following test:

Individual RBL-2H3-cells (a turnout cell line related to the mast cells) adhering to glass slides are used.

The cultivation and attachment of the RBL-2H3-cells are carried out by the method described by HIDE and BEAVEN (1991). In order to sensitise the adhesive RBL-2H3-cells the cells are incubated for 2 hours at ambient temperature with a 1:2000 diluted commercial gammaglobulin E-solution against a dinitrophenol-bovine serum albumin complex (DNP-BSA-antigen). The cells are then washed. By the addition of 0.1 ml of DNP-BSA-solution (10 μg/ml) there is a massive immunological cell activation which is mediated by a cytoplasmic $Ca^{2+}$-overload. The fluorometric calcium measurement in the cytoplasm of individual adhering RBL-2H3-cells is carried out analogously to the method described by KUDO and OGURA (1986) for neuronal cells, which is also explained hereinbefore in this specification.

The comparison used in these investigations is (10 μM) chromoglycate which brings about an approximately 50% inhibition of the antigen-induced cell activation.

In this test the above-mentioned compounds demonstrate % H values which are comparable with the values specified hereinbefore.

Tests on microcultures of various human tumour cell lines using the tetrazolium assay in order to determine the antiproliferative effect of the substances according to the invention surprisingly showed that the compound tested was 5 to 100 times more potent than the comparison substance Verapamil.

The antiproliferative effectiveness of the test substances was determined by means of the MTT test described by MOSMANN (J. IMMUNOL. METH. 65: 55–63, 1983), DENIZOT et al. (J. IMMUNOL. METH. 89: 271–277, 1986) and J. ELIASON et al. (INT. J. CANCER 46: 113–117, 1990). (MTT=[3—(4,5-dimethylthiazol-2-yl)2,5-diphenyl-tetrazolium bromide] produced by CHEMICON Inc. El Segundo, Calif., USA). This indicator is metabolised only by living cells with intact mitochondria into a blue formazane product. The following human tumour cell lines were used in our test: A 549 (adenocarcinoma of the lung), A 431 (epidermal carcinoma of the vulva), PC 3 (adenocarcinoma of the prostate), SK BR 3 (adenocarcinoma of the breast), HT 29 (CX1 1) (adenocarcinoma of the colon) and K 562 (chronic myeloid leukaemia cell).

The test was carried out on microtitre plates. Each well contained 100 μl of a cell suspension ($0.2 \times 10^6$ cells per ml). The incubation medium used was RPMI 1640 with 10% heat-inactivated foetal calves' serum and 50 μg/ml of gentamycin. The cell suspensions were incubated for 0, 24, 48 or 72 hours in air with a humidity at saturation point in a $CO_2$ (5%)/air (95%) mixture at 37° C., incubated in the presence and absence of variable concentrations of antiproliferative test substances. The test substances were dissolved in DMSO (final dilution: 0.1%). Then 10 μl of MTT-solution (3 mg/ml) were added, followed after 3 hours by 100 μl of an isopropanol solution containing 0.08N HCl. After a further hour, the light absorption at 570 nm (comparative wavelength 630 nm) was determined in a microplate reader. The light absorption is directly proportional to the number of living cells. The half-maximum inhibitory concentrations of the substances tested were 1 μg/ml.

The vasospasmolytic effectiveness of the above-mentioned functional endothelin and Thapsigargin antagonists were confirmed on an isolated blood vessel preparation: coronary perfusion was continuously quantified, on retrogressively perfused, spontaneously beating LANDEN-DORFF hearts taken from rats, by means of electromagnetic flow measurement (apparatus supplied by Hugo Sachs Elektronik, MARCH). This measuring apparatus could be used to record the extent, duration and pattern of vascular spasms with a high degree of accuracy. If perfusion is carried out with 100 nM endothelin concentration, the coronary perfusion flow is reduced from 11 to 5 ml/min. The restriction in perfusion can be reversed by means of the substances according to the invention. The potencies of the compounds according to the invention with regard to Thapsigargin inhibition on fura-2-charged RBL-hm 1-cells or the effectiveness of endothelin-inhibition on fura-2-charged HL 60 cells correlates dearly with the vasospasmolytic effectiveness of the test substances detected on the Langendorff preparation. It can be concluded from this that, underlying the vasospasmolytic endothelin antagonism of the substances tested, there is a blockade of the unselective cation channels.

The compounds may be administered both enterally and parenterally. The suggested dose for oral use ranges from 0.1 to 500 mg of active substance per dose and, for intravenous use, from 0.05 to 150 mg per dose. The desired therapeutic dose depends on the indication and form of administration and can be determined experimentally.

Suitable forms include, for example, tablets, capsules, suppositories, solutions, syrups, emulsions, aerosols or dispersible powders. Tablets may be produced, for example, by ruling the active substance or substances with known excipients, e.g. inert diluents such as calcium carbonate, calcium phosphate or lactose, disintegrants such as corn starch or alginic add, binders such as starch or gelatine, lubricants such as magnesium stearate or talc and/or agents for obtaining delayed release, such as carboxypolymethylene, carboxymethylcellulose, cellulose acetate phthalate or polyvinylacetate. The tablets may also consist of several layers.

Coated tablets may be produced analogously by coating cores made in the same way as the tablets with substances conventionally used for tablet coatings, e.g. collidone or shellack, gum arabic, talc, titanium dioxide or sugar. In order to obtain delayed release or avoid incompatibilities, the core may also consist of several layers. Similarly, the tablet coating may consist of several layers to achieve delayed release, whilst the excipients mentioned for the tablets may be used.

Syrups containing the active substances or combinations of active substances according to the invention may additionally contain a sweetener such as saccharin, cyclamate, glycerol or sugar as well as a flavour enhancer, e.g. a flavouring such as vanillin or orange extract. They may also contain suspension adjuvants or thickeners such as sodium carboxymethylcellulose, wetting agents, e.g. condensation products of fatty alcohols with ethylene oxide or preservatives such as p-hydroxybenzoates.

Injectable solutions are produced in the usual way, e.g. by adding preservatives such as p-hydroxybenzoates or stabilisers such as alkali metal salts of ethylene dismine tetraacetic add, and are then transferred into injection vials or ampoules.

Capsules containing one or more active substances or combinations of active substances may be prepared for example by mixing the active substances with inert carriers such as lactose or sorbitol and encapsulating them in gelatine capsules.

Suitable suppositories may be produced for example by mixing with carriers provided for this purpose, such as neutral fats or polyethyleneglycol or derivatives thereof.

Processes for preparing the compounds of formula I are described in European Patent Applications 252 299 and U.S. Pat. No. 5,614,516, to which reference is hereby made.

Examples of Pharmaceutical Preparations a) Coated tablets 1 tablet core contains:

| | |
|---|---|
| Active substance of general formula I | 30.0 mg |
| Lactose | 100.0 mg |
| Corn starch | 75.0 mg |
| Gelatine | 3.0 mg |
| Magnesium stearate | 2.0 mg |
| | 210.0 mg |

Preparation

The active substance mixed with lactose and corn starch is granulated with a 10% aqueous gelatine solution through a 1 mm mesh screen, dried at 40° C. and rubbed through a screen once more. The granules thus obtained are mixed with magnesium stearate and compressed. The cores produced in this way are coated in the usual manner with a coating consisting of an aqueous suspension of sugar, titanium dioxide, talc and gum arabic. The finished coated tablets are polished with beeswax.

b) Tablets

| | |
|---|---|
| Active substance of general formula I | 30.0 mg |
| Lactose | 100.0 mg |
| Corn starch | 70.0 mg |
| Soluble starch | 7.0 mg |
| Magnesium stearate | 3.0 mg |
| | 210.0 mg |

Preparation

The active substance and magnesium stearate are granulated with an aqueous solution of the soluble starch, the granules are dried and internately mixed with lactose and corn starch. The mixture is then compressed into tablets weighing 210 mg.

c) Capsules

| | |
|---|---|
| Active substance according to formula I | 20.0 mg |
| Lactose | 230.0 mg |
| Corn starch | 40.0 mg |
| Talc | 10.0 mg |
| | 300.0 mg |

Preparation

The active substance, lactose and corn starch are first combined in a mixer and then in a grinding machine. The mixture is returned to the mixer, thoroughly combined with the talc and mechanically packed into hard gelatine capsules.

d) Tablets

| Active substance according to the invention | 40.0 mg |
| --- | --- |
| Lactose | 100.0 mg |
| Corn starch | 50.0 mg |
| Colloidal silica | 2.0 mg |
| Magnesium stearate | 3.0 mg |
| total | 195.0 mg |

Preparation

The active substance is mixed with some of the excipients and granulated with a solution of the soluble starch in water. After the granules have dried the remaining excipients are added and the mixture is compressed to form tablets.

e) Coated tablets

| Active substance according to the invention | 20.0 mg |
| --- | --- |
| Lactose | 100.0 mg |
| Corn starch | 65.0 mg |
| Colloidal silica | 2.0 mg |
| Soluble starch | 5.0 mg |
| Magnesium stearate | 3.0 mg |
| total | 195.0 mg |

Preparation

The active substance and excipients are compressed to form tablet cores as described in Example a) 1 and these are then coated in the usual way with sugar, talc and gum arabic.

f) Suppositories

| Active substance according to the invention | 50.0 mg |
| --- | --- |
| Lactose | 250.0 mg |
| Suppository mass q.s. ad | 1.7 g |

Preparation

The active substance and lactose are mixed together and the mixture is uniformly suspended in the molten suppository mass. The suspensions are poured into chilled moulds to form suppositories weighing 1.7 g.

g) Ampoules

| Active substance according to the invention | 20.0 mg |
| --- | --- |
| Sodium chloride | 5.0 mg |
| Twice distilled water q.s. ad | 2.0 ml |

Preparation

The active substance and the sodium chloride are dissolved in twice distilled water and the solution is transferred under sterile conditions into ampoules.

h) Ampoules

| Active substance according to the invention | 10.0 mg |
| --- | --- |
| Sodium chloride | 7.0 mg |
| Twice distilled water q.s. ad | 1.0 ml | i) Drops

| Active substance according to the invention | 0.70 g |
| --- | --- |
| Methyl p-hydroxybenzoate | 0.07 g |

-continued

| Propyl p-hydroxybenzoate | 0.03 g |
| --- | --- |
| Demineralised water q.s. ad | 100.00 ml |

Preparation

The active substance and preservatives are dissolved in demineralised water, the solution is filtered and transferred into 100 ml vials.

What is claimed is:

1. A compound of formula (I)

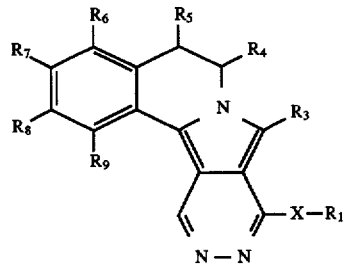

wherein

X is O, S or NHO;

$R_1$ has one of the following meanings:

a) $C_{3-7}$-cycloalkyl;

b) a straight-chained or branched alkyl group having 1 to 10 or an alkenyl or alkynyl group having 2 to 10 carbon atoms, which alkyl, alkenyl or alkynl group may be substituted by hydroxy, $C_{1-4}$-alkoxy, halogen, $NH_2$, NH-alkyl having 1 to 2 carbon atoms, N,N-di($C_{1-2}$)alkylamino, NH-acyl having 2 to 4 carbon atoms, 1 or 2 $C_{3-7}$-cycloalkyl groups, phenoxy, 1 or 2 phenyl groups (wherein the phenyl ring or rings or phenoxy may in turn be mono- or disubstituted by halogen, $CF_3$, $C_{1-4}$-alkyl, $C_{1-2}$-alkoxy, NH-alkyl having 1 to 2 carbon atoms, N,N-dialkyl having 1 to 2 carbon atoms, $NH_2$, N-acyl having 2 to 3 carbon atoms, $-OCH_2O-$, ($C_1$ or $C_2$) alkylsulphonylamino, phenoxy or benzyloxy), furyl or thienyl;

$R_3$, $R_4$ and $R_5$, which may be identical or different, are hydrogen or a $C_{1-4}$-alkyl group;

$R_7$ and $R_8$, which may be identical or different, are hydroxy; $C_{1-4}$-alkoxy; or $C_{1-4}$-alkylthio;

$R_6$ and $R_9$, which may be identical or different, are hydrogen; hydroxy; $C_{1-4}$-alkoxy; $C_{1-4}$-alkylthio;

or 2 adjacent substituents of the substituents $R_6$, $R_7$, $R_8$ and $R_9$ together form the group $-O-(CH_2)_{1\ or\ 2}-O-$ and the other 2 substituents are as hereinbefore defined, or a pharmaceutically acceptable salt thereof, with the exception of compounds of formula I as hereinbefore defined wherein $XR_1$ is the group $SR_1$ wherein $R_1$ is $C_{1-5}$ alkyl or benzyl.

2. A compound as recited in claim 1, wherein X is O, S or NHO;

$R_1$ has one of the following meanings:

a) $C_{3-7}$-cycloalkyl;

b) a straight-chained or branched alkyl group having 1 to 5 or an alkenyl or alkynyl group having 2 to 5 carbon atoms, which which alkyl, alkenyl or alkynl group may be substituted by hydroxy, $C_{1-4}$-alkoxy, halogen, $NH_2$, NH-alkyl having 1 to 2 carbon atoms, N,N-di($C_{1-2}$)alkylamino, NH-acyl having 2 to 4 carbon atoms, $C_{3-7}$-cycloalkyl, 1 or 2 phenyl groups (wherein the phenyl ring or rings may in turn be mono- or disubstituted by halogen, $CF_3$ $C_{1-4}$-alkyl, $C_{1-2}$-alkoxy, NH-alkyl having 1 to 2 carbon atoms, N,N-dialkyl having 1 to 2 carbon atoms, $NH_2$, N-acyl having 2 to 3 carbon atoms, ($C_1$ or $C_2$) alkylsulphonylamino or benzyloxy), furyl or thienyl;

$R_3$, $R_4$ and $R_5$, which may be identical or different, are hydrogen or a $C_{1-4}$-alkyl group;

$R_7$ and $R_8$, which may be identical or different, are hydroxy; $C_{1-4}$-alkoxy; or $C_{1-4}$-alkylthio and $R_6$ and $R_9$, which may be identical or different, are hydrogen; hydroxy; $C_{1-4}$-alkoxy; $C_{1-4}$-alkylthio, or 2 adjacent substituents of the substituents $R_6$, $R_7$, $R_8$ and $R_9$ together form the group —O—$(CH_2)_{1\ or\ 2}$—O— and the other 2 substituents are as hereinbefore defined.

3. A compound as recited in claim 1, wherein $R_1$ has one of the following meanings:

a) $C_{3-7}$-cycloalkyl;

b) a straight-chained or branched alkyl group having 1 to 5 or an alkenyl or alkynyl group having 2 to 5 carbon atoms, which which alkyl, alkenyl or alkynl group may be substituted by hydroxy, $C_{1-4}$-alkoxy, halogen, $NH_2$, NH-alkyl having 1 to 2 carbon atoms, N,N-di($C_{1-2}$)alkylamino, NH-acyl having 2 to 4 carbon atoms, $C_{3-7}$-cycloalkyl, phenyl (wherein the phenyl ring may in turn be mono- or disubstituted by halogen, $C_{1-2}$-alkyl, $C_{1-2}$-alkoxy, NH-alkyl having 1 to 2 carbon atoms, N,N-dialkyl having 1 to 2 carbon atoms, $NH_2$, N-acyl having 2 to 3 carbon atoms or ($C_1$ or $C_2$) alkylsulphonylamino, furyl or thienyl;

$R_3$, $R_4$ and $R_5$, which may be identical or different, are hydrogen or a $C_{1-4}$-alkyl group;

$R_7$ and $R_8$, which may be identical or different, are hydroxy; $C_{1-4}$-alkoxy; or $C_{1-4}$-alkylthio and $R_6$ and $R_9$, which may be identical or different, are hydrogen; hydroxy; $C_{1-4}$-alkoxy; $C_{1-4}$-alkylthio.

4. A compound as recited in claim 1, wherein $R_1$ is a straight-chained or branched $C_{1-4}$-alkyl group which is substituted by $C_{3-7}$-cycloalkyl, thienyl or 1 or 2 unsubstituted phenyl groups or by a substituted phenyl group.

5. A compound as recited in claim 4, wherein $R_1$ is ($C_{1-4}$) alkylcyclohexyl.

6. A compound as recited in claim 5, wherein $R_1$ is —$CH_2$—$C_6H_{11}$.

7. A compound as recited in claim 4, wherein $R_1$ is ($C_{1-4}$)alkylphenyl, wherein the phenyl group is unsubstituted or is mono- or disubstituted by F, Cl, $CF_3$, methyl, ethyl, methoxy or ethoxy.

8. A compound as recited in claim 1, wherein $R_3$, $R_4$, $R_5$, $R_6$ and $R_9$ are hydrogen and $R_7$ and $R_8$ are $C_{1-4}$-alkoxy or $R_7$ and $R_8$ together are —$OCH_2O$— or —$OCH_2CH_2O$—.

9. A compound as recited in claim 8, wherein $R_7$ and $R_8$ are methoxy.

10. A compound as recited in claim 1, wherein X is O, S or NHO; $R_3$, $R_4$, $R_5$, $R_6$ and $R_9$ are hydrogen; $R_7$ and $R_8$ are $C_{1-4}$-alkoxy or $R_7$ and $R_8$ together are —$OCH_2O$— or —$OCH_2CH_2O$— and $R_1$ is

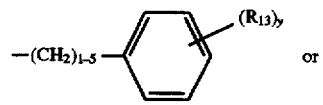 or

—$(CH_2)_{1\ or\ 2}CH(C_6H_5)_2$, wherein $R_{13}$ is $CF_3$, $C(CH_3)_3$ or —$OCH_2C_6H_5$ and y is 1 or 2, or.

11. A compound as recited in claim 10, wherein $R_1$ is the group

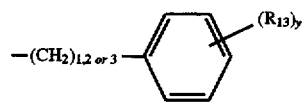

wherein $R_{13}$ and y are defined as in claim 11.

12. A compound as recited in claim 10, wherein $R_7$ and $R_8$ are methoxy.

13. A compound as recited in claim 1, wherein X is S.

14. A compound as recited in claim 1, wherein $R_1$ is one selected from the group consisting of:

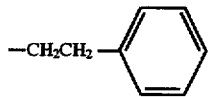,

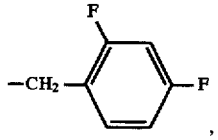,

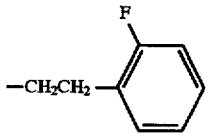,

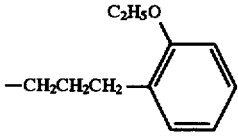,

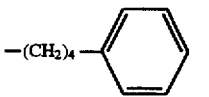,

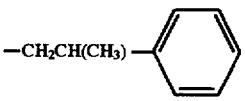,

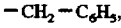,

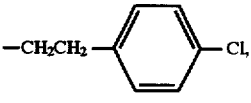,

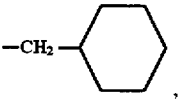,

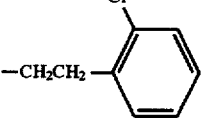,

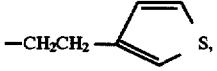

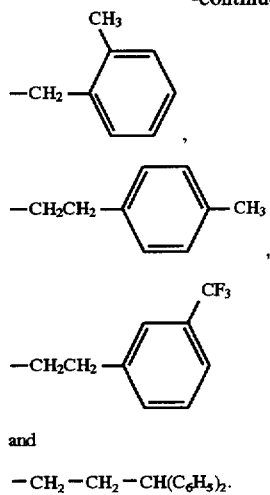

and

−CH₂−CH₂−CH(C₆H₅)₂.

15. A compound as recited in claim 1 wherein R₁ is selected from the group consisting of:

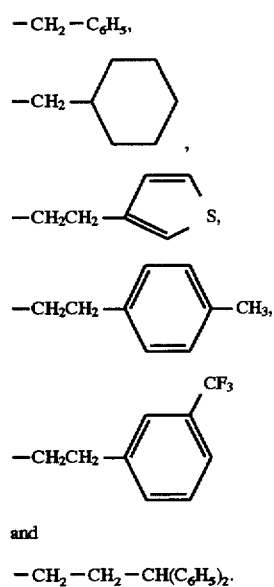

and

−CH₂−CH₂−CH(C₆H₅)₂.

16. A compound as recited in claim 10, wherein R₇ and R₈ are methoxy and R₁ is selected from the group consisting of:

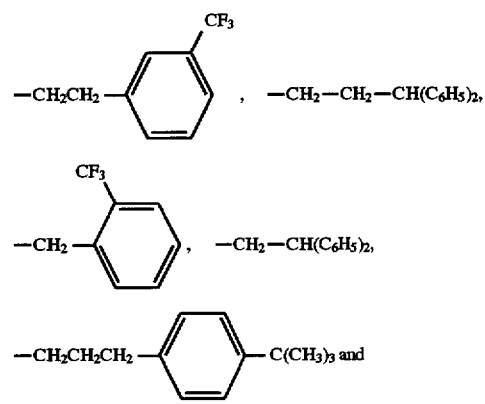

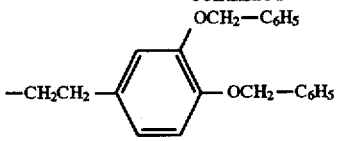

17. A compound as recited in claim 1, wherein X is O, S or NHO; R₃, R₄, R₅, R₆ and R₉ are hydrogen; R₇ and R₈ represent methoxy; and, R₁ is selected from the group consisting of:

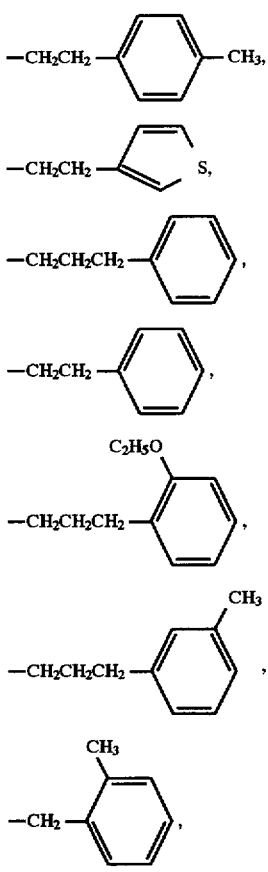

-continued

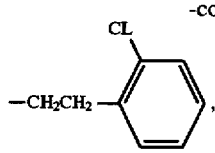

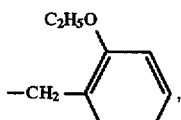

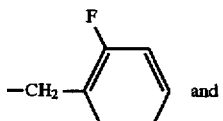
and

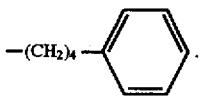

18. A compound as recited in claim 17, wherein $R_1$ is selected from the group consisting of:

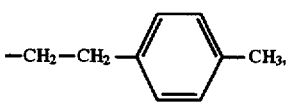

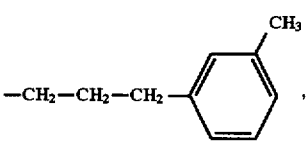

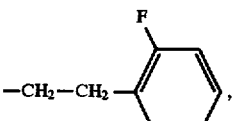

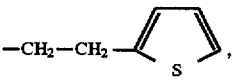

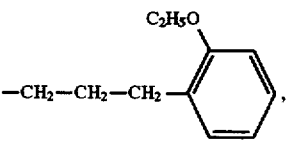

-continued

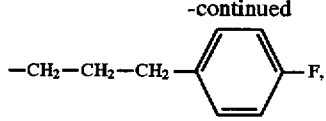

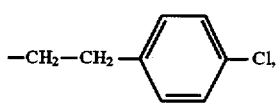

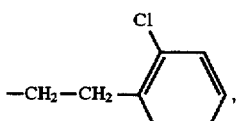

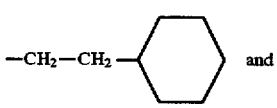 and

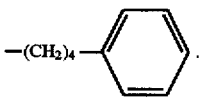

19. A compound as recited in claim 1, wherein X is O, S or NHO; $R_3$, $R_4$, $R_5$, $R_6$ and $R_9$ are hydrogen; $R_7$ and $R_8$ are methoxy; and $R_1$ is selected from the group consisting of:

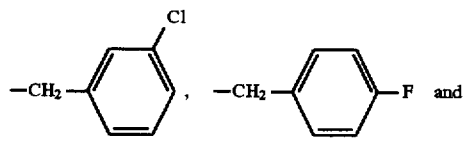

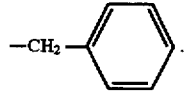

20. A pharmaceutical composition comprising a compound in accordance with claim 1 and a pharmaceutically acceptable carrier.

* * * * *